US010836794B2

(12) United States Patent
Myasoedov et al.

(10) Patent No.: US 10,836,794 B2
(45) Date of Patent: Nov. 17, 2020

(54) GROUP OF PEPTIDES FOR TREATING FEMALE SEXUAL DYSFUNCTION

(71) Applicant: "IVIX" Ltd., Moscow (RU)

(72) Inventors: Nikolai Fedorovich Myasoedov, Moscow (RU); Lyudmila Alexandrovna Andreeva, Moscow (RU); Dmitry Viktorovich Golikov, Moscow (RU); Mikhail Yurievich Lomonosov, Moscow (RU)

(73) Assignee: "IVIX" LTD., Moscow (RU)

( * ) Notice: Subject to any disclaimer, the term of this patent is extended or adjusted under 35 U.S.C. 154(b) by 0 days.

(21) Appl. No.: 16/344,248

(22) PCT Filed: Oct. 2, 2017

(86) PCT No.: PCT/RU2017/050099
§ 371 (c)(1),
(2) Date: Apr. 23, 2019

(87) PCT Pub. No.: WO2018/080349
PCT Pub. Date: May 3, 2018

(65) Prior Publication Data
US 2019/0263865 A1 Aug. 29, 2019

(30) Foreign Application Priority Data

Oct. 24, 2016 (RU) .............................. 2016112342

(51) Int. Cl.
*C07K 7/06* (2006.01)
*A61P 15/00* (2006.01)
*A61K 9/00* (2006.01)
*A61K 47/18* (2017.01)
*C07K 5/08* (2006.01)
*A61K 38/00* (2006.01)

(52) U.S. Cl.
CPC ............. *C07K 7/06* (2013.01); *A61K 9/0043* (2013.01); *A61K 47/186* (2013.01); *A61P 15/00* (2018.01); *C07K 5/08* (2013.01); *C07K 5/0827* (2013.01); *A61K 38/00* (2013.01)

(58) Field of Classification Search
None
See application file for complete search history.

(56) References Cited

U.S. PATENT DOCUMENTS

| 3,778,426 | A | 12/1973 | Najjar et al. |
| 5,932,548 | A | 8/1999 | Deghenghi |
| 5,955,421 | A | 9/1999 | Deghenghi |
| 6,177,405 | B1 | 1/2001 | Nishioka et al. |
| 6,211,156 | B1 | 4/2001 | Argiolas et al. |
| 8,883,741 | B2 | 11/2014 | Myazsiedov et al. |
| 2009/0111161 | A1 | 4/2009 | Jones et al. |
| 2010/0095987 | A1 | 4/2010 | Jones et al. |
| 2010/0190722 | A1 | 7/2010 | Bevec et al. |
| 2010/0197572 | A1 | 8/2010 | Bevec et al. |
| 2010/0204143 | A1 | 8/2010 | Bevec et al. |
| 2010/0204148 | A1 | 8/2010 | Bevec et al. |
| 2010/0210534 | A1 | 8/2010 | Bevec |
| 2010/0210567 | A1* | 8/2010 | Bevec .................... A61K 38/12 514/6.9 |
| 2010/0273700 | A1 | 10/2010 | Bevec et al. |
| 2010/0286028 | A1 | 11/2010 | Bevec et al. |
| 2011/0081711 | A1 | 4/2011 | Bevec et al. |
| 2012/0129791 | A1 | 5/2012 | Jones et al. |

FOREIGN PATENT DOCUMENTS

| CN | 101302246 | 11/2008 |
| CN | 104274818 A | 1/2015 |
| EA | 013948 B1 | 8/2010 |

(Continued)

OTHER PUBLICATIONS

Galasik-Bartoszek et al. (Int . J. Peptide Protein Res. 38, 1991, 176-180) (Year: 1991).*
Marple et al. (Otolaryngol Head Neck Surg. Jan. 2004;130(1):131-41) (Year: 2004).*
Communication (International Preliminary Report on Patentability) issued by the International Searching Authority in International Application No. PCT/RU2017/050099, dated Apr. 30, 2019, 4 pages total.
Communication (International Search Report and Written Opinion) issued by the International Searching Authority in International Application No. PCT/RU2017/050099, dated Dec. 28, 2017, 6 pages total.

(Continued)

*Primary Examiner* — Sergio Coffa
(74) *Attorney, Agent, or Firm* — Troutman Pepper Hamilton Sanders LLP

(57) ABSTRACT

The invention relates to the chemistry of peptides, pharmacology and medicine, and specifically to a new group of peptides having the property of stimulating sexual and genital function and having increased storage stability. For this purpose, peptides of general formula (I) are proposed: A-Thr-Lys-Hyp-B-C-D-X, (SEQ ID NO: 8), in which A is 0, Met, Met(0), Thr, Ala, His, Phe, Lys, Gly; B is 0, Gly, Asp, Trp, Gln, Asn, Tyr, Hyp, Arg; C is 0, Arg, Phe, Tyr, Gly, His, Hyp, Lys; D is 0, Val, Gly, Tyr, Trp, Phe, His; X is OH, OCH$_3$, NH$_2$; where 0 is the absence of an amino acid residue, provided that if A≠0, then B and/or C and/or D≠0, if B≠0, then C and/or D≠0, excluding the tetrapeptides, as well as the peptides Phe-Thr-Lys-Hyp-Gly, (SEQ ID NO: 9), Thr-Lys-Hyp-Hyp-Arg (SEQ ID NO: 10) and Thr-Lys-Hyp-Arg-Gly (SEQ ID NO: 11). The invention also relates to pharmaceutical compositions containing the indicated peptides, as well as to the use of the above indicated compositions for the treatment of women with severely decreased libido or with totally absent libido, orgasmic dysfunction, sexual dysfunction not caused by organic disorders or diseases, HSDD, FSAD or FSIAD, and to a method of treating and/or preventing female sexual dysfunction.

12 Claims, 3 Drawing Sheets

Specification includes a Sequence Listing.

(56) References Cited

FOREIGN PATENT DOCUMENTS

| EA | 200900804 A1 | 8/2010 |
| --- | --- | --- |
| EP | 2465521 A1 | 6/2012 |
| EP | 2876113 A2 | 5/2016 |
| JP | 2012528856 A | 11/2012 |
| JP | 2015515855 A | 6/2015 |
| JP | 2018118973 A | 8/2018 |
| RU | 1124544 C | 1/1995 |
| RU | 2058791 C1 | 4/1996 |
| RU | 2130030 C1 | 5/1999 |
| RU | 2155065 C1 | 8/2000 |
| RU | 2264823 C2 | 1/2004 |
| RU | 2252779 C1 | 5/2005 |
| RU | 2290195 C1 | 12/2006 |
| RU | 2318533 C1 | 3/2008 |
| RU | 2404793 C1 | 11/2010 |
| RU | 2411249 C1 | 2/2011 |
| RU | 2507212 C2 | 2/2014 |
| RU | 2507212 C2 * | 2/2014 |
| UA | 28397 U | 12/2007 |
| WO | 9422460 A1 | 10/1994 |
| WO | 01034171 A2 | 5/2001 |
| WO | 2009033678 A2 | 3/2009 |
| WO | 2009058679 A1 | 7/2009 |
| WO | 2010140926 A1 | 12/2010 |
| WO | 2013151467 A2 | 10/2013 |

OTHER PUBLICATIONS

Galasik-Bartoszek, U. et al., "[Hyp3] -tuftsin ([Hyp3]-TU) Synthesis and Biological Activity" International Journal of Peptide & Protein Research (1991) vol. 38, Issue 1, pp. 176-180.

Andreeva et al., The Perspectives of Development of New Peptide Preparations for Clinical Use Which Have Anti-Infective and Immune-Modulating Activity, Infekc. Immun. (20011) vol. 1, No. 2, pp. 171-176.

Arletti et al., "Sexual Impotence is Associated with a Reduced Production of Oxytocin and with an Increased Production of Opioid Peptides in the Paraventricular Nucleus of Male Rate" Neuroscience Letters 233 (1997) pp. 65-68.

Ashmarin et al., "A Comparative Analysis of the Distribution of Glyprolines After Their Administration by Different Ways" Russian Journal of Bioorganic Chemistry (2008) pp. 415-420.

Ashmarin et al., "Natural and Hybrid ("Chimeric") Stable Regulatory Glyproline Peptides" Pathophysiology (2005) vol. 11, pp. 179-185.

Auriault et al., "Characterization and Synthesis of a Macrophage Inhibitory Peptide from the Second Constant Domain of Human Immunolobulin G" FEBS Letters, Mar. 1983, vol. 153, No. 1, pp. 11-12.

Canadian Communication issued by the Canada Patent Office in Canada Application No. 2,868,820 dated Mar. 14, 2019, 5 pages total.

Cantor et al., "Chronic Fluxetine Inhibits Sexual Behavior in the Male Rat: Reversal with Oxytocin" Psychopharmacology (1999) vol. 144, pp. 355-362.

Chinese Communication issued by the State Intellectual Property Office of the People's Republic of China in Chinese Patent Application No. 201380028491.4 dated Dec. 26, 2017.

Chinese Communication issued by the State Intellectual Property Office of the People's Republic of China in Chinese Patent Application No. 201380028491.4 dated Jun. 8, 2017.

Chinese Communication issued by the State Intellectual Property Office of the People's Republic of China in Chinese Patent Application No. 201380028491.4 dated Nov. 23, 2018, 9 pages total.

Chipens G.I. et al., "Elongated and Cyclic Analogues of Tuftsin and Rigin" Peptides, Proceedings of the Sixteenth European Peptide Symposium (1981) pp. 445-450.

Communication (International Preliminary Report on Patentability) issued by the International Searching Authority in International Application No. PCT/RU2017/050112, dated Apr. 30, 2019, 5 pages total.

Communication (International Search Report and Written Opinion) issued by the International Searching Authority in International Application No. PCT/RU2017/050112, dated Jan. 31, 2018, 15 pages total.

Communication Pursuant to Rule 164(1) EPC, Partial Supplemental European Search Report issued in European Patent Application No. 13772776.4 dated Oct. 26, 2016, 8 pages.

Czabak-Garbacz et al., "Influence of Long-Term Treatment with Tuftsin Analogue TP-7 on the Anxiety-Phobic States and Body Weight" Pharmacological Reports (2006) vol. 58, pp. 562-567.

Dagan, S. et al., "Tuftsin Analogues: Synthesis, Structure-Function Relationships, and Implications for Specificity of Tuftsin's Bioactivity" Journal of Medicinal Chemistry (1986) vol. 29, pp. 1961-1968.

Diamond et al., "Co-Administration of Low Doses of Intranasal PT-141, A Melanocortin Receptor Agonist, and Sildenafil to Men with Erectile Dysfunction Results in an Enhanced Erectile Response" Urology (2005) vol. 65, No. 4, pp. 755-759.

English-language abstract of Chinese Patent Publication No. CN101302246; Database WPI, Week 200912, Thompson Scientific, Long, GB; AN 2009-641118 XP002686138, & CN 101302246 A (Inst Toxicant & Medicament Acad Military) Nov. 12, 2008 (Nov. 12, 2008) Abstract.

European Communication (Communication Pursuant to Article 94(3) EPC) issued by the European Patent Office in European Patent Application No. 13772776.4, dated Dec. 18, 2017.

European Communication (Communication Pursuant to Article 94(3) EPC) issued by the European Patent Office in European Patent Application No. 13772776.4, dated Sep. 25, 2018.

European Communication (Extended European Search Report) issued by the European Patent Office in European Patent Application No. 17866053.6, dated Mar. 12, 2020.

European Extended Search Report issued in European Patent Application No. 13772776.4 dated Feb. 1, 2017, 11 pages.

First Office Action issued in Chinese Application No. 201380028491.4 dated Sep. 27, 2016, English Translation Thereof, 16 pages.

GenScript Peptide Calculator, Peptide Sequence TKP, obtained from https://www.genscript.com on Aug. 21, 2015.

Indian Communication issued by the Indian Patent Office in India Application No. 8984/DELNP/2014 dated Mar. 30, 2019, 8 pages total.

International Preliminary Report on Patentability dated Dec. 6, 2011, which issued during prosecution of Intetnational Application No. PCT/RU2010/000285.

International Preliminary Report on Patentability issued in PCT/RU2013-000433 dated Oct. 1, 2014 and English Translation Thereof, 4 pages.

International Search Report dated Sep. 18, 2013, which issued during prosecution of International Application No. PCT/RU2010/000285.

International Search Report issued by the International Searching Authority in International Application No. PCT/RU2013/000433 dated Oct. 31, 2013, which corresponds to the present application.

Japanese Communication issued by the Japanese Patent Office in Japanese Patent Application No. 2015-503152 dated Jan. 22, 2019, 21 pages total.

Japanese Communication issued by the Japanese Patent Office in Japanese Patent Application No. 2015-503152 dated Mar. 7, 2017.

Japanese Communication issued by the Japanese Patent Office in Japanese Patent Application No. 2015-503152 dated Oct. 24, 2017.

Japanese Communication issued by the Japanese Patent Office in Japanese Patent Application No. 2018-030815 dated Jan. 15, 2019, 21 pages total.

Kavai et al., "Chemotactic and Stimulating Effect of Tuftsin and its Analogues on Human Monocytes" Immunology Letters (1981) vol. 2, pp. 219-224.

Kolomin et al., "Expression of Inflammation-Related Genes in Mouse Spleen Under Tuftsin Analog Selank" Regulatory Peptides (2011) vol. 170, pp. 18-23.

Korean communication issued by the Korean Intellectual Property Office in Korea Application No. 10-2014-7030301 dated Jan. 10, 2020, 13 pages total.

(56) References Cited

OTHER PUBLICATIONS

Korean communication issued by the Korean Intellectual Property Office in Korea Application No. 10-2014-7030301 dated Jun. 8, 2019, 13 pages total.
Kozlovskaya et al., "A Comparative Study of the Effect of Tuftsin Fragments on Passive Avoidance Learning Characteristics" Pharmaceutical Chemistry Journal (2001) vol. 35, No. 3, pp. 121-123.
Kozlovskaya et al., "Comparison Study of Series of Tuftsin's Fragments of Short-Time and Durable Action on the Index of Conditional Reactions of Passive Avoidance" Chimiko-Pharmac. Zh. (2001) vol. 35, pp. 3-5.
Kozlovskaya et al., "Selank and Short Peptides of the Tuftsin Family in the Regulation of Adaptive Behavior in Stress" Neuroscience and Behavioral Physiology (2003) vol. 33, No. 9, pp. 853-860.
Kozlovskaya et al., "Selank and Short Peptides of Tuftsin Derivatives in Regulation of Adaptive Behaviour of Animal in Stress" Ross. Fiziol. Zh. I. M. Sechenova. (2002) vol. 88, pp. 751-761.
Kumar et al., "Sexual Behaviour in Normal and Neurotic Females" Indian J. Psychiat. (1984) vol. 26, No. 3, pp. 213-218.
Mezo et al., "Synthesis, Conformation, and Immunoreactivity of New Carrier Molecules Based on Repeated Tuftsin-Like Sequence" Biopolymers (2004) pp. 645-656.
Nair R. et al., "Interactions of Radiolabeled Tuftsin with Human Neutrophils" Immunochemistry (1978) pp. 901-907.
Patil et al., "Cross-Species Analysis of the Mammalian β-Defensin Gene Family: Presence of Syntenic Gene Clusters and Preferential Expression in the Male Reproductive Tract" Comparative Genomics (2005) pp. 5-17.
Pavlov, T.S. "Anti-Ulcer Effects of Selank and its Fragments" Abstract of Ph.D. Thesis, Moscow (2006) (Translated from "Protivoiazvennye effekty selanka i ego fragmentov, Avtoreferat dissertatsii na soiskanie uchenoi stepeni kandidata biologicheskikh nauk").
Semenova et al., "Use of Selank to Correct Measures of Integrative Brain Activity and Biogenic Amine Levels in Adult Rates Resulting from Antenatal Hypoxia" Neuroscience and Behavioral Physiology (2008) vol. 38, No. 2, pp. 203-207. (Translated from Rossiiskii Fiziologicheskii Zhurnal imeni I.M. Schenova, vol. 92, No. 11, pp. 1332-1338, 2006).
Semion et al., "Antinociceptive Action of the SP1-4 Tetrapeptide and of Some Tuftsin Analogs" Pol. J. Pharmacol. Pharm. (1990) vol. 42, pp. 393-401.

Semple et al., "Duplication and Selection in the Evolution of Primate β-Definsin Genes" Genome Biology (2003) vol. 4, pp. R31.1-R31.11.
Seredinin et al., "The Study of Anxiolytic Activity of Tuftsin Analogue in Inbred Mice with Different Types of Emotional-Stress Reaction" Institute of Pharmocology, Russian Academy of Medical Sciences, Moscow, Zhurnal VND (1998) vol. 48, No. 1, pp. 153-160. (English Translation).
Shevchenko et al., "Synthesis of Tritium-Labeled Selank" Radiochemistry (2006) vol. 48, No. 3, pp. 296-300.
Sollertinskaya et al., "Compensatory and Antiamnestic Effects of Heptapeptide Selank in Monkeys" Journal of Evolutionary Biochemistry and Physiology (2008) vol. 44, No. 3, pp. 332-340.
Supplementary European Search Report dated Nov. 15, 2012, which issued during prosecution of EP 10783644.7.
UniProtKB/Swiss-Prot: Q8WTQ1.2; D104A_HUMAN; Jul. 2015; pp. 1-3.
Wang, et al., "Protective Role of Tuftsin Fragment 1-3 in an Animal Model of Intracerebral Hemorrhage" Annals of Neurology (2003) vol. 54, No. 5, pp. 655-664.
Zolotarev, et al., "Evenly Tritium-Labeled Peptides in Study of Peptide in Vivo and In Vitro Biodegration" Russian Journal of Bioorganic Chemistry (2006) vol. 32, No. 2, pp. 166-173. (Corresponds to Russian-language reference Zolotarev et al., Ravnomerno mechenie tritium peptide v issledovaniyah poi h biodegradacii in vivo i in vitro, Bi000rganicheskaya Khimiya, 2006, 32(2): 183-191).
The Peptides International, "FAQs: A General Guideline for Storage & Handling of Peptides", https://www.pepnet.com/res/uploads/case_studies/peptideguidelines.pdf downloaded Apr. 30, 2020, 2 pages total.
Kushwaha, S.K.S., et al., "Advances in Nasal Trans-Mucosal Drug Delivery" Journal of Applied Pharmaceutical Science (2011) vol. 1, No. 7, pp. 21-28.
U.S. Communication (Non-Final Office Action) issued by the United States Patent and Trademark Office in U.S. Appl. No. 16/344,293, dated Jun. 8, 2020, 9 pages total.
European Communication (Extended European Search Report) issued by the European Patent Office in European Patent Application No. 17865481.0, dated Jun. 16, 2020, 6 pages total.
Japanese Communication issued by the Japanese Patent Office in Japanese Patent Application No. 2019-129091 dated Aug. 4, 2020, 6 pages total.

* cited by examiner

SEQUENCE LISTING

```
<160> NUMBER OF SEQ ID NOS: 14

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Lys Pro Arg Pro Gly Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Met(O), Thr, Ala, His, Phe, Lys, Gly, or
      not present
<220> FEATURE:
<221> NAME/KEY: MOD_RES
<222> LOCATION: (5)..(5)
<223> OTHER INFORMATION: Gly, Asp, Trp, Gln, Asn, Tyr, Pro, Arg, or not
      present
<220> FEATURE:
<221> NAME/KEY: MOD_RES
<222> LOCATION: (6)..(6)
<223> OTHER INFORMATION: Arg, Phe, Tyr, Gly, His, Pro, Lys, or not
      present
<220> FEATURE:
<221> NAME/KEY: MOD_RES
<222> LOCATION: (7)..(7)
<223> OTHER INFORMATION: Val, Gly, Tyr, Trp, Phe, His, or not present
<220> FEATURE:
<223> OTHER INFORMATION: See specification as filed for detailed
      description of substitutions and preferred embodiments

<400> SEQUENCE: 2

Xaa Thr Lys Pro Xaa Xaa Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Thr Lys Pro Gly
1               5
```

-continued

```
<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Lys Pro Pro Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Lys Pro Arg Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Lys Pro Arg Pro
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Lys Pro Arg Pro Phe
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met, Met(O), Thr, Ala, His, Phe, Lys, Gly, or
      not present
<220> FEATURE:
<221> NAME/KEY: MOD_RES
<222> LOCATION: (4)..(4)
<223> OTHER INFORMATION: Hydroxyproline
<220> FEATURE:
<221> NAME/KEY: MOD_RES
<222> LOCATION: (5)..(5)
<223> OTHER INFORMATION: Gly, Asp, Trp, Gln, Asn, Tyr, Hyp, Arg, or not
      present
<220> FEATURE:
<221> NAME/KEY: MOD_RES
```

```
<222> LOCATION: (6)..(6)
<223> OTHER INFORMATION: Arg, Phe, Tyr, Gly, His, Hyp, Lys, or not
      present
<220> FEATURE:
<221> NAME/KEY: MOD_RES
<222> LOCATION: (7)..(7)
<223> OTHER INFORMATION: Val, Gly, Tyr, Trp, Phe, His, or not present
<220> FEATURE:
<223> OTHER INFORMATION: See specification as filed for detailed
      description of substitutions and preferred embodiments

<400> SEQUENCE: 8

Xaa Thr Lys Pro Xaa Xaa Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Hydroxyproline

<400> SEQUENCE: 9

Phe Thr Lys Pro Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline
<220> FEATURE:
<221> NAME/KEY: MOD_RES
<222> LOCATION: (4)..(4)
<223> OTHER INFORMATION: Hydroxyproline

<400> SEQUENCE: 10

Thr Lys Pro Pro Arg
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline

<400> SEQUENCE: 11

Thr Lys Pro Arg Gly
1               5

<210> SEQ ID NO 12
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline

<400> SEQUENCE: 12

Thr Lys Pro Arg Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline

<400> SEQUENCE: 13

Thr Lys Pro Arg Pro Phe
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline
<220> FEATURE:
<221> NAME/KEY: MOD_RES
<222> LOCATION: (5)..(5)
<223> OTHER INFORMATION: Hydroxyproline
<220> FEATURE:
<221> NAME/KEY: MOD_RES
<222> LOCATION: (7)..(7)
<223> OTHER INFORMATION: Hydroxyproline

<400> SEQUENCE: 14

Thr Lys Pro Arg Pro Gly Pro
1               5
```

GROUP OF PEPTIDES FOR TREATING FEMALE SEXUAL DYSFUNCTION

CROSS-REFERENCE TO RELATED APPLICATIONS

This application is a U.S. National Phase application under 35 U.S.C. § 371 of International Patent Application No. PCT/RU2017/050099, filed on Oct. 2, 2017, which claims priority to Russia Patent Application No. RU 2016112342, filed on Oct. 24, 2016, all of which applications are incorporated herein by reference in their entireties.

FIELD OF TECHNOLOGY

The invention relates to peptide chemistry, pharmacology, and medicine, and specifically to a new group of peptides having the property of stimulating sexual and genital function and having increased storage stability, to their use in obtaining pharmaceutical compositions, and also to the pharmaceutical compositions containing these peptides.

PRIOR ART

Female sexual dysfunction (FSD) relates to various disorders in sexual function resulting in loss of interest in sexual activity, recurrent inability to achieve or sustain sexual excitement, and inability to reach orgasm after adequate excitation.

Many different methods of treatment have been proposed and employed for the treatment of female sexual dysfunction, with a variable degree of success. These treatment methods either were not completely successful, or their side effects were difficult to tolerate. The most effective drug used in clinical practice is Flibanserin. Nevertheless, there is a need to develop new drugs for the treatment of female sexual dysfunction.

Therapeutic peptides are widely used in medical practice. Pharmaceutical compositions containing such therapeutic peptides need to have a shelf life of several years, in order to be suitable for practical use. However, peptide compositions by their very nature are unstable, due to their susceptibility to chemical and physical degradation. Chemical degradation involves a change in the covalent bonds, such as oxidation, hydrolysis, racemization or cross linking. Physical degradation involves conformational changes with regard to the native structure of the peptide which may lead to aggregation, precipitation or adsorption on surfaces.

It has previously been established that the heptopeptide "Selank" of general formula Thr-Lys-Pro-Arg-Pro-Gly-Pro (SEQ ID NO: 1), a synthetic analogue of the endogenous peptide tuftsin, can be used as a drug for prevention and treatment of genital and sexual dysfunctions (RU2404793).

From the document RU2507212 there is known a group of peptides with the property of stimulating the genital and sexual functions:

A-Thr-Lys-Pro-B-C-D-X (SEQ ID NO: 2),
in which A is 0, Met, Met(0), Thr, Ala, His, Phe, Lys, Gly;
B is 0, Gly, Asp, Trp, Gln, Asn, Tyr, Pro, Arg;
C is 0, Arg, Phe, Tyr, Gly, His, Pro, Lys;
D is 0, Val, Gly, Tyr, Trp, Phe, His;
X is OH, OCH$_3$, NH$_2$; where 0 is the absence of an amino acid residue, provided that
if A≠0, then B and/or C and/or D≠0, if B≠0, then C and/or D≠0, excluding the tetrapeptides, as well as the peptides Phe-Thr-Lys-Pro-Gly (SEQ ID NO: 3), Thr-Lys-Pro-Arg (SEQ ID NO: 4) and Thr-Lys-Pro-Arg-Gly (SEQ ID NO: 5).

It has been established that synthesized peptides, especially the tripeptide Thr-Lys-Pro, the pentapeptides Thr-Lys-Pro-Arg-Pro (SEQ ID NO: 6), and the hexapeptide Thr-Lys-Pro-Arg-Pro-Phe (SEQ ID NO: 7), corresponding to the general formula A-Thr-Lys-Pro-B-C-D-X (SEQ ID NO: 2), can be recommended as stimulators of genital and sexual function.

All the peptides of the document RU2507212 of general formula A-Thr-Lys-Pro-B-C-D-X (SEQ ID NO: 2) (except for the tetrapeptides, and also the peptides Phe-Thr-Lys-Pro-Gly (SEQ ID NO: 3), Thr-Lys-Pro-Pro-Arg (SEQ ID NO: 4) and Thr-Lys-Pro-Arg-Gly (SEQ ID NO: 5)), which are recommended as stimulators of the genital and sexual function, have a common feature, namely, the presence in the structure of the peptide molecule of the tripeptide Thr-Lys-Pro. However, the pharmaceutical forms based on all these peptides have an acceptable stability when kept only at temperature up to +10° C., which reduces their commercial potential, and causes inconvenience in the storing, use, distribution and marketing of the drug.

Since the peptides described above have limits on their storage conditions and shelf life, there is a need to reduce these limitations on the storage conditions and to increase the degree of compliance of the drugs (the degree of compliance of the behavior of the patient and the recommendations given by the doctor).

Thus, there exists a need to create new peptides with the property of stimulating the genital and sexual function and having good efficacy and improved stability during storage.

DISCLOSURE OF THE INVENTION

The problem which the present invention solves is the development and creation of new peptides with the property of stimulating the genital and sexual function, having enhanced efficacy and stability during storage, and promising for use in clinical practice.

The technical result to be achieved by this invention is the development and production of new peptides with the property of stimulating the genital and sexual function, having enhanced efficacy and increased stability during storage, which in turn makes it possible to reduce the limitations on the storage conditions of the drugs based on the peptides according to the invention. Furthermore, an additional technical result is a faster speed of onset of the positive (therapeutic) effect due to the action of the peptides according to the invention, as compared to their peptide analogues.

This technical result is achieved by the development and production of compounds of general formula (I):

A-Thr-Lys-Hyp-B-C-D-X (SEQ ID NO: 8)    formula (I)

or their pharmaceutically acceptable salts,
in which A is 0, Met, Met(0), Thr, Ala, His, Phe, Lys, Gly;
B is 0, Gly, Asp, Trp, Gln, Asn, Tyr, Hyp, Arg;
C is 0, Arg, Phe, Tyr, Gly, His, Hyp, Lys;
D is 0, Val, Gly, Tyr, Trp, Phe, His;
X is OH, OCH$_3$, NH$_2$;
where 0 is the absence of an amino acid residue, provided that if A≠0, then B and/or C and/or D≠0, if B≠0, then C and/or D≠0, excluding the tetrapeptides, as well as the peptides Phe-Thr-Lys-Hyp-Gly (SEQ ID NO: 9), Thr-Lys-Hyp-Hyp-Arg (SEQ ID NO: 10) and Thr-Lys-Hyp-Arg-Gly (SEQ ID NO: 11).

It has been discovered surprisingly that the presence of hydroxyproline (Hyp) instead of Pro in the peptides according to the invention significantly lowers the level of oxidation and degradation of the peptides, which allows the drugs based on these peptides to be kept at room temperature. Moreover, the use of Hyp instead of Pro in the peptides does not affect their safety. Furthermore, it has been established surprisingly that the use of the peptides according to the invention is able to significantly shorten the course of treatment of the patient because the effect due to the action of these peptides is achieved twice as fast as compared to the peptide analogues described in the document RU2507212.

The present invention also relates to the use of the peptides according to the invention to obtain a pharmaceutical composition characterized by the property of stimulating sexual and genital function for the treatment of female sexual dysfunction.

The invention also includes pharmaceutical compositions having the property of stimulating sexual and genital function for the treatment of female sexual dysfunction, HSDD, F SAD or FSIAD, containing a therapeutically effective quantity of at least one which is the subject matter of the present invention and at least one pharmaceutically acceptable excipient. In particular, the excipient may be a vehicle, a preservative, and/or a solvent.

In certain variant embodiments of the invention, the pharmaceutical compositions according to the invention are a liquid pharmaceutical form. In some variant embodiments of the invention, the liquid pharmaceutical form is a solution for intranasal administration. In certain preferred variant embodiments of the invention, the pharmaceutical composition is an aqueous solution including the following components in concentrations, g/l, of the peptide of general formula (I)—2 to 20;
benzalkonium chloride—0.095 to 0.105.

In certain variant embodiments of the invention, the sexual dysfunction is characterized by decreased libido or a total absence of libido. In certain particular variant embodiments of the invention, the sexual dysfunction is characterized by decreased or absent sexual desire or attraction. In preferred variant embodiments of the invention, the sexual dysfunction is hypolibidemia. In other variant embodiments of the invention, the sexual dysfunction is orgasmic dysfunction.

In certain variant embodiments of the invention, the female sexual dysfunction is sexual aversion and absence of sexual satisfaction, inadequate or absent genital response, vaginism of non-organic origin, dyspareunia of non-organic origin.

The invention also includes other kinds of sexual dysfunction not caused by organic disorders or diseases (somatic or psychological).

Yet another aspect of the invention is a method of administering the compositions according to the invention, characterized in that the composition is given intranasally, and in certain variants the composition is given intranasally in the form of a spray.

The invention also relates to a method of treatment and/or prevention of female sexual dysfunction, involving the administering of a pharmaceutical composition according to the invention to a patient.

The invention also includes the producing of compounds of general formula (I).

DETAILED DISCLOSURE OF THE INVENTION

Definition and Terms

For a better understanding of the present invention, several terms used in the present invention are presented below.

Female sexual dysfunction is a disturbance in the course of the sexual responses at the stage of arousal, in the primary phase, the stage of orgasm or release, and painfulness during intercourse. The disorder, including subjective and objective factors, prevents the obtaining of satisfaction. Furthermore, it sometimes leads to infertility or is more or less connected with it.

Libido (from the Latin: "attraction, desire, passion") means sexual desire or sexual instinct. It is the psychological component of sexual attraction.

Hypolibidemia, anaphrodisia is the absence or loss of sexual attraction. Hypolibidemia is one of the sexual dysfunctions not caused by organic disorders or diseases (code F52.0 of MKB-10).

HSDD is hypoactive sexual desire disorder.

FSAD is female sexual arousal disorder.

FSIAD is female sexual interest/arousal disorder.

Compliance is adherence to the treatment, the degree of correspondence between the patient's behavior and the recommendations given by the doctor.

Met(0) in the present document means methionine sulfoxide.

Implementing of the Invention

The possibility of objective manifestation of the technical result when using the invention is confirmed by reliable data presented in the examples, containing information of an experimental nature. It should be understood that these and all the examples presented in the materials of the application are not limiting and are given only as an illustration of the present invention.

Survey of Methods of Obtaining the Peptides Per the Invention

EXAMPLE 1

Synthesis of the Tripeptide Thr-Lys-Hyp

Figure 1:
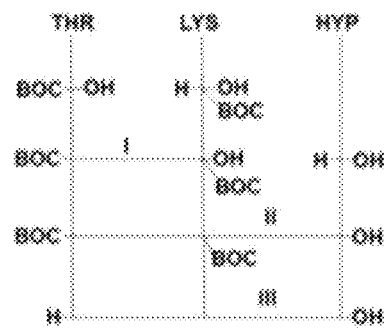
FIG. 1. Diagram for the synthesis of the tripeptide Thr-Lys-Hyp.

The synthesis of the tripeptide Thr-Lys-Hyp is done according to the diagram presented in FIG. 1. The synthesis of the tripeptide Thr-Lys-Hyp is done using modern protective groups and methods of creating a peptide bond in solution that are known from the prior art. To create the peptide bond, the method of activated esters and the method of TBA (tetrabutylammonium) salts are used. The peptide chain is grown in stages.

EXAMPLE 2

Synthesis of the Pentapeptide
Thr-Lys-Hyp-Arg-Hyp (SEQ ID NO: 12)

Figure 2:
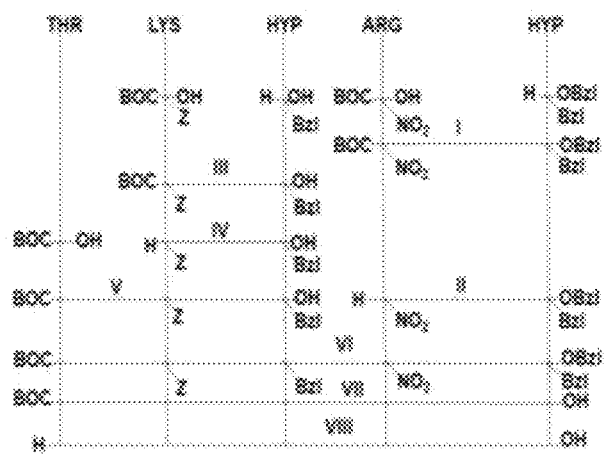
FIG. 2. Diagram for the synthesis of the pentapeptide Thr-Lys-Hyp-Arg-Hyp (SEQ ID NO: 12).

The synthesis of the pentapeptide Thr-Lys-Hyp-Arg-Hyp (SEQ ID NO: 12) is done according to the diagram presented in FIG. 2. The synthesis of the pentapeptide Thr-Lys-Hyp-Arg-Hyp (SEQ ID NO: 12) is done using modern protective groups and methods of creating a peptide bond in solution that are known from the prior art. To create the peptide bond, the method of activated esters and the carbodiimide method are used. Both a stagewise growth of the peptide chain and a block method are used.

EXAMPLE 3

Synthesis of the Hexapeptide
Thr-Lys-Hyp-Arg-Hyp-Phe (SEQ ID NO: 13)

Figure 3:
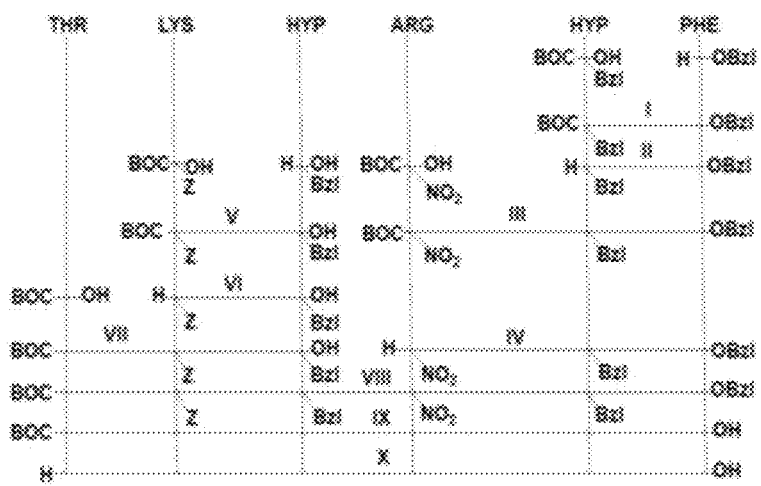
FIG. 3. Diagram for the synthesis of the hexapeptide Thr-Lys-Hyp-Arg-Hyp-Phe (SEQ ID NO: 13).
Figure 4:
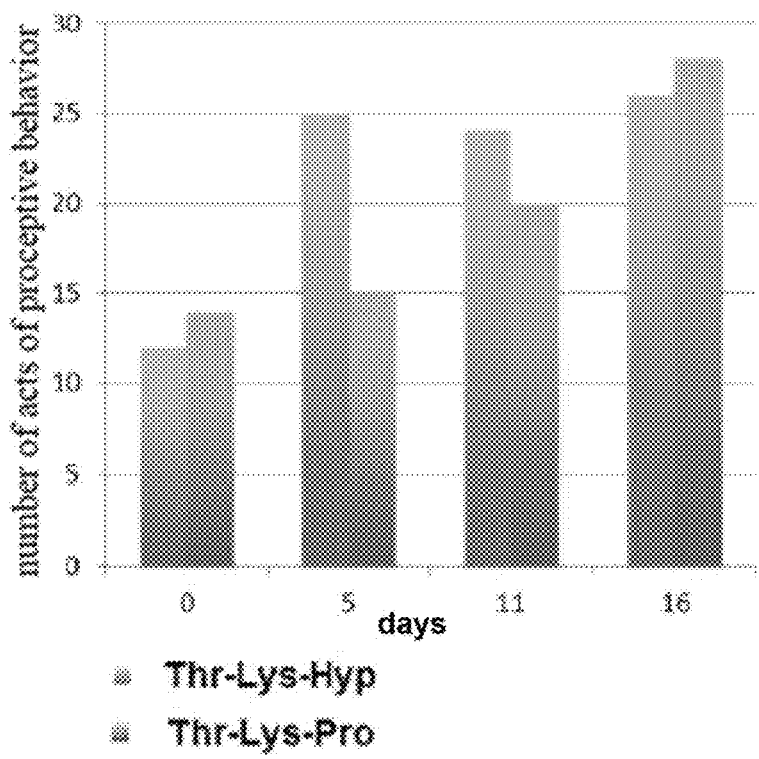
FIG. 4. Comparison of the influence of the peptide Thr-Lys-Hyp with the peptide Thr-Lys-Pro on the proceptive behavior of the rat.
Figure 5:
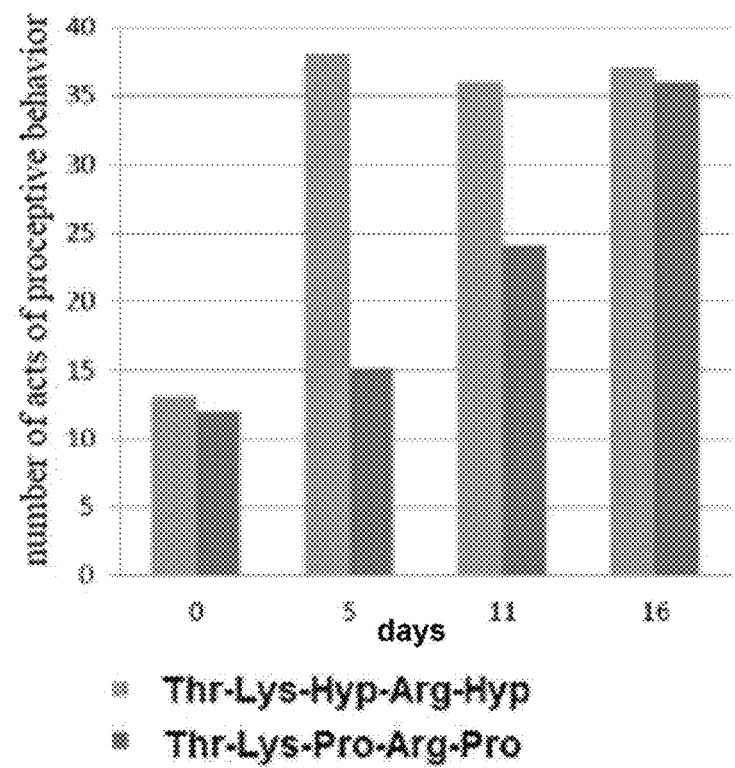
FIG. 5. Comparison of the influence of the peptide Thr-Lys-Hyp-Arg-Hyp (SEQ ID NO: 12) with the peptide Thr-Lys-Pro-Arg-Pro (SEQ ID NO: 6) on the proceptive behavior of the rat.
Figure 6:
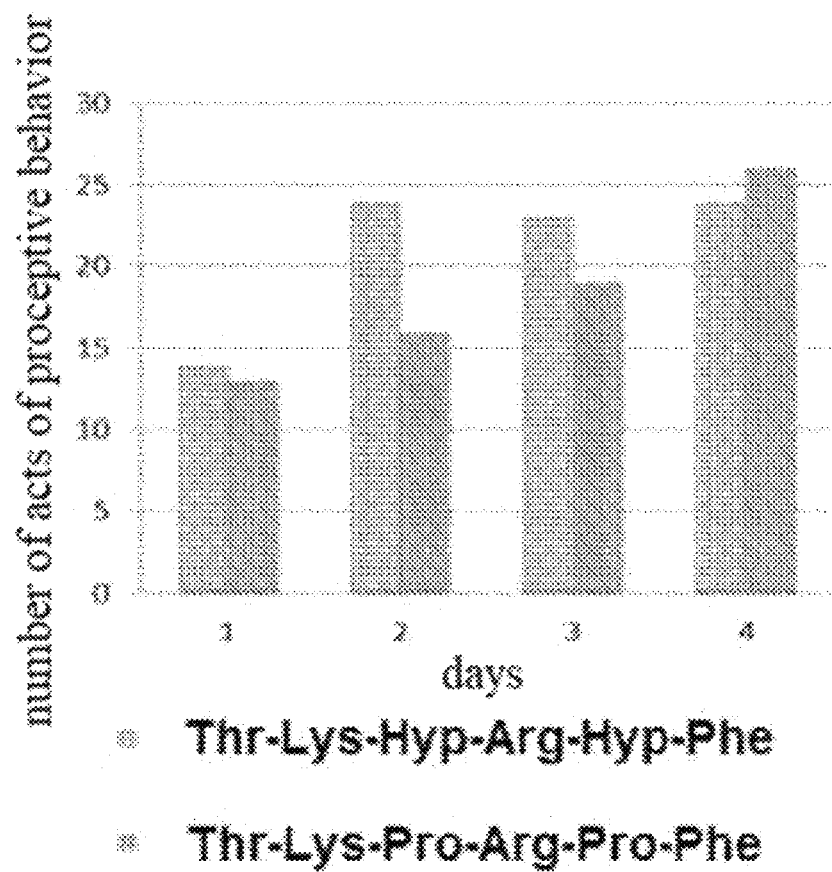
FIG. 6. Comparison of the influence of the peptide Thr-Lys-Hyp-Arg-Hyp-Phe (SEQ ID NO: 13) with the peptide Thr-Lys-Pro-Arg-Pro-Phe (SEQ ID NO: 7) on the proceptive behavior of the rat.

The synthesis of the hexapeptide Thr-Lys-Hyp-Arg-Hyp-Phe (SEQ ID NO: 13) is done according to the diagram presented in FIG. 3. The synthesis of the hexapeptide Thr-Lys-Hyp-Arg-Hyp-Phe (SEQ ID NO: 13) is done using modern protective groups and methods of creating a peptide bond in solution that are known from the prior art. To create the peptide bond, the method of TBA salts, the method of activated esters, the carbodiimide method and the method of mixed anhydrides are used. Both a stagewise growth of the peptide chain and a block method are used.

For the synthesis of the peptides presented in examples 1-3, derivatives of both protected and free L-amino acids are used. The solvents used during the synthesis of the peptides are dehydrated in corresponding manner. The boiling down of the solutions is done on a vacuum evaporator at 40° C. The obtained intermediate compounds and the synthesized peptides are checked with the aid of TLC analysis on plates of silica gel from the Silufol company (Czech Republic). The compounds obtained are detected by spraying the plate with a solution of ninhydrin and (or) o-tolidine. Verification of the homogeneity of the obtained peptides is done with the aid of high-efficiency liquid chromatography (HELC) on a liquid microcolumn chromatograph Millichrom A-02. The structure of the synthesized peptides is characterized with the aid of mass spectrometry on a mass spectrometer from the firm ThermoElectron LCQ Advantage MAX.

The results of the chromatographic and mass spectrometry analysis of the peptides according to the invention, presented in examples 1-3, are shown in table 1. The form of the gradient for separating the synthesized peptides by the HELC method is shown in table 2.

TABLE 1

Primary chromatographic and mass spectrometry parameters of the peptides of the invention.

| No. | Peptide | Molecular weight, MW, g/mol | Chromatographic characteristics | | Mass spectrometry characteristics | |
|---|---|---|---|---|---|---|
| | | | Retention time, Tr, min | Purity, % | *[M+H]$^+$ | **Fragmenting of mol. peak |
| 1 | Thr-Lys-Hyp | 360 | 3.02 | 98.1 | 361 | 343(100), 230(44), 260(16) |
| 2 | Thr-Lys-Hyp-Arg-Hyp (SEQ ID NO: 12) | 629 | 4.56 | 98.5 | 630 | 612(100), 230(63), 499(32) |
| 3 | Thr-Lys-Hyp-Arg-Hyp-Phe (SEQ ID NO: 13) | 776 | 10.31 | 97.9 | 777 | 759(100), 612(71), 499(43) |

Note:
*Molecular peak corresponding to the ion [M+H]$^+$
**The most intensive ions forming upon fragmenting of the molecular peak at energy of ion collisions with helium atoms of 35 eV.

Table 1 presents the data (HELC) obtained on the liquid microcolumn chromatograph Millichrom A-02 and the mass spectrometry characteristics of the synthesized peptides obtained with the aid of the mass spectrometer ThermoElectron LCQ Advantage MAX.

The chromatography conditions that were developed make it possible to easily obtain chromatographically pure products.

Chromatography Conditions for Analysis of the Peptides:
Chromatograph Millichrom A-02
Column: Prontosil 120-5Cl8aq, 2*75 mm
Eluent A: 0.2M LiClO$_4$+5 mM HClO$_4$
Eluent B: methanol

TABLE 2

Form of the gradient for separation of the synthesized peptides.

| Time | Eluent B, % |
|---|---|
| 0 | 5 |
| 16.5 | 80 |

Flow rate: 150 mcl/min;
Detector wavelength set: 210, 220, 230, 240 nm.
Mass Spectrometry Analysis Conditions:
Instrument: ThermoElectron LCQ Advantage MAX;
Ion source: electrospray; direct feeding to the source of a peptide solution with concentration of 10 mcg/ml in 0.1% acetic acid at a rate of 5 mcl/min;
Fragmenting of the molecular ion at 35 eV by the method of ion collisions (He). Temperature of source 250° C., ionization potential +3.5 kV.

The Method of Therapeutic Use of the Compounds

The subject matter of the present invention also includes the administering to a subject in need of the corresponding treatment of a therapeutically effective quantity of a peptide of the general formula (I).

The term "therapeutically effective quantity" is understood to be that quantity of a peptide which, when administered as a monotherapy or a combined therapy, elicits a therapeutic effect sufficient for the treatment of female sexual dysfunction. When the peptide of the invention is used in combined therapy, the term "therapeutically effective quantity" refers to the combination of the quantity of active ingredients the taking of which leads to the preventive or therapeutic effect when taken in succession or at the same time. The exact quantity required may vary from one subject to another depending on the age and the general condition of the patient, the severity of the illness, the technique of administering the drug, combined treatment with other drugs, and so on.

The invention also relates to pharmaceutical compositions which contain peptides according to the invention and at least one pharmaceutically acceptable excipient, especially a vehicle, a preservative, and/or a solvent, which can be given to the patient along with the peptides constituting the essence of the present invention, and not disturbing the biological activity of said peptide, and being nontoxic when given in doses adequate to deliver the effective quantity of the peptide.

Pharmaceutically Acceptable Peptide Derivatives

The compounds of the present invention may exist in the free form in the course of their processing or, if so required, in the form of a pharmaceutically acceptable salt or other derivative. The term "pharmaceutically acceptable salt" used here pertains to those salts which, in the context of a medical evaluation, are suitable for use in contact with human and animal tissues without excessive toxicity, irritation, allergic reaction, and so forth, and which have a reasonable risk/benefit ratio. The salts may be obtained in the course of the synthesis, the separation or the purification of the compounds according to the invention, and they may also be obtained separately, by the reacting of the free acid or the free base of the compound of the invention with a suitable base or acid, respectively. Examples of pharmaceutically acceptable, nontoxic salts of acids are, in particular, the acetate, the hydrochloride, the citrate, and others.

Pharmaceutical Compositions

The invention also relates to pharmaceutical compositions containing at least one of the compounds described here (or a prodrug form, a pharmaceutically acceptable salt or other pharmaceutically acceptable derivative) and one or more pharmaceutically acceptable vehicles, solvents, and/or fillers. Said compositions may also contain one or more additional therapeutic agents. On the other hand, a compound of the present invention may be given to a patient requiring the corresponding therapy in combination with one or more other therapeutic regimens.

The pharmaceutical compositions proposed in the present invention contain compounds of the present invention together with pharmaceutically acceptable vehicles, which may include any given solvents, diluents, dispersions or suspensions, surfactants, isotonic agents, preservatives, and so forth, suitable for the specific dosage form. Except for such cases where the medium of the usual vehicles is incompatible with the compound of the invention, for example upon appearance of any unwanted biological effects or other unwanted interactions with any other component(s) of the pharmaceutical composition, the use of such compositions is within the scope of the present invention.

Investigations of the Stability of Pharmaceutical Forms Containing Peptides Having the Property of Stimulating the Genital and Sexual Functions This experiment investigated the stability of compositions containing peptides according to the invention. The results of the investigations are illustrated by the example of several peptides according to the invention containing hydroxyproline, in particular Thr-Lys-Hyp (SEQ ID NO: 12), Thr-Lys-Hyp-Arg-Hyp (SEQ ID NO: 13), Thr-Lys-Hyp-Arg-Hyp-Phe and Thr-Lys-Hyp-Arg-Hyp-Gly-Hyp (SEQ ID NO: 14).

The peptides described in RU2507212 were also obtained, in particular Thr-Lys-Pro, Thr-Lys-Pro-Arg-Pro (SEQ ID NO: 6), Thr-Lys-Pro-Arg-Pro-Phe (SEQ ID NO: 7) and Thr-Lys-Pro-Arg-Pro-Gly-Pro (SEQ ID NO: 1).

From the compounds obtained, a liquid pharmaceutical form (a solution) was prepared, including the peptide and the preservative benzalkonium chloride with the following ratio of components: 0.2 and 0.01 mass %, respectively, water the rest. Samples were placed in storage at two temperature regimes, namely, +4° C. and +25° C. Investigation of the stability of the peptides was carried out after 1, 3, 6, 12, and 24 months of storage. In the investigation of the samples for stability, the quantity of single impurities and the total quantity of impurities were evaluated, testifying to the degradation of the peptides. The pharmaceutical requirements of the company for impurities are: any single impurity, not more than 1.5%; total content of impurities, not more than 3.0%. If the content of impurities exceeded the above indicated values, the pharmaceutical form was deemed to have failed the test for stability. The results of the investigation are presented in table 3.

TABLE 3

Results of the investigation of the stability of pharmaceutical forms containing peptides with the property of stimulating genital and sexual function at +4° C. and +25° C.

| Peptide formula and storage temperature | Stored for 1 month Single/total impurities (%) | Stored for 3 months Single/total impurities (%) | Stored for 6 months Single/total impurities (%) | Stored for 12 months Single/total impurities (%) | Stored for 24 months Single/total impurities (%) |
|---|---|---|---|---|---|
| Thr-Lys-Pro, at +4° C. | 0.051/0.13 | 0.053/0.135 | 0.3/0.9 | 0.9/1.7 | 1.2/2.2 |
| Thr-Lys-Pro, at +25° C. | 0.06/0.1 | 0.13/0.25 | 1.7/3.1 | — | — |
| Thr-Lys-Pro-Arg-Pro (SEQ ID NO: 6), at +4° C. | 0.042/0.09 | 0.042/0.93 | 0.09/1 | 0.8/1.5 | 1.1/1.9 |
| Thr-Lys-Pro-Arg-Pro (SEQ ID NO: 6), at +25° C. | 0.067/0.54 | 0.19/0.9 | 1.4/3.0 | 4/6 | — |
| Thr-Lys-Pro-Arg-Pro-Phe (SEQ ID NO: 7), at +4° C. | 0.054/0.17 | 0.09/0.18 | 0.5/1.1 | 0.9/1.3 | 1.6/2,9 |
| Thr-Lys-Pro-Arg-Pro-Phe (SEQ ID NO: 7), at +25° C. | 0.11/0.19 | 0.9/1.1 | 1.9/3.5 | — | — |
| Thr-Lys-Pro-Arg-Pro-Gly-Pro (SEQ ID NO: 1), at +4° C. | 0.05/0.17 | 0.07/0.2 | 0.8/1.4 | 1/1.7 | 2/3.7 |
| Thr-Lys-Pro-Arg-Pro-Gly-Pro (SEQ ID NO: 1), at +25° C. | 0.065/0.13 | 0.9/1.2 | 1.7/3.1 | — | — |
| Thr-Lys-Hyp, at +4° C. | 0.034/0.09 | 0.035/0.11 | 0.036/0.2 | 0.09/0.3 | 0.1/0.9 |
| Thr-Lys-Hyp, at +25° C. | 0.052/0.11 | 0.052/0.9 | 0.2/1 | 0.3/1.2 | 0.8/1.8 |
| Thr-Lys-Hyp-Arg-Hyp (SEQ ID NO: 12), at +4° C. | 0.03/0.09 | 0.03/0.09 | 0.04/0.1 | 0.07/0.2 | 0.1/0.7 |
| Thr-Lys-Hyp-Arg-Hyp (SEQ ID NO: 12), at +25° C. | 0.046/0.14 | 0.047/0.15 | 0.1/0.7 | 0.2/0.9 | 0.9/1.2 |
| Thr-Lys-Hyp-Arg-Hyp-Phe (SEQ ID NO: 13), at +4° C. | 0.067/0.15 | 0.068/0.15 | 0.08/0.2 | 0.1/0.3 | 0.9/1.9 |
| Thr-Lys-Hyp-Arg-Hyp-Phe (SEQ ID NO: 13), at +25° C. | 0.032/0.09 | 0.033/0.09 | 0.09/0.6 | 0.4/0.8 | 1.3/2.7 |

TABLE 3-continued

Results of the investigation of the stability of pharmaceutical forms containing peptides with the property of stimulating genital and sexual function at +4° C. and +25° C.

| Peptide formula and storage temperature | Stored for 1 month Single/total impurities (%) | Stored for 3 months Single/total impurities (%) | Stored for 6 months Single/total impurities (%) | Stored for 12 months Single/total impurities (%) | Stored for 24 months Single/total impurities (%) |
|---|---|---|---|---|---|
| Thr-Lys-Hyp-Arg-Hyp-Gly-Hyp (SEQ ID NO: 14), at +4° C. | 0.049/0.12 | 0.05/0.12 | 0.06/0.14 | 0.09/0.3 | 0.1/1.1 |
| Thr-Lys-Hyp-Arg-Hyp-Gly-Hyp (SEQ ID NO: 14), at +25° C. | 0.069/0.14 | 0.07/0.5 | 0.09/0.9 | 0.3/1.1 | 1.2/2.6 |

It emerges from table 3 that the peptides containing hydroxyproline instead of proline were much more successful in passing the test for stability during storage (content of impurities in the samples with peptides containing hydroxyproline is several times less than that in the samples with peptides containing proline), and this at both temperatures. Thus, the peptides containing hydroxyproline are more stable to degradation than their peptide analogues (RU2507212), which makes it possible to keep the finished pharmaceutical forms based on the peptides of the invention at temperature up to +25° C. for at least 24 months.

Investigation of the Efficacy of the Peptides of the Invention as a Means of Stimulating the Genital and Sexual Functions In order to confirm the efficacy as a means of stimulating the genital and sexual functions, peptides according to the invention were synthesized, in particular the tripeptide Thr-Lys-Hyp, the pentapeptide Thr-Lys-Hyp-Arg-Hyp (SEQ ID NO: 12), and the hexapeptide Thr-Lys-Hyp-Arg-Hyp-Phe (SEQ ID NO: 13), and tests were performed as to the efficacy in vivo on the relevant preclinical model (Lordoz test). Furthermore, the efficacy of the group of peptides Thr-Lys-Pro, Thr-Lys-Pro-Arg-Pro (SEQ ID NO: 6), and Thr-Lys-Pro-Arg-Pro-Phe (SEQ ID NO: 7) was also investigated.

The efficacy of the aforementioned groups of peptides was investigated in a dose of 100 mcg/rat with respect to the sexual behavior of female rats. The sexual behavior was registered over the course of 0-16 days in ovarioectomized, hormonally stimulated females in the case of direct contact with sexually active males and in the case when no such contact was possible. It was found that the peptides of the group Thr-Lys-Hyp, Thr-Lys-Hyp-Arg-Hyp (SEQ ID NO: 12), and Thr-Lys-Hyp-Arg-Hyp-Phe (SEQ ID NO: 13) increase the intensity of proceptive behavior of the females from 12±4 to 24±4-36±6 acts during the time of the registration (p=0.028, Wilkinson's criterion). The results testify to an increase in sexual motivation under the action of the peptides Thr-Lys-Hyp, Thr-Lys-Hyp-Arg-Hyp (SEQ ID NO: 12), and Thr-Lys-Hyp-Arg-Hyp-Phe (SEQ ID NO: 13). The results of the test are presented in table 4.

TABLE 4

Results of investigating the efficacy of the peptides of the invention as a means of stimulating the genital and sexual functions and the peptides described in RU2507212, on a relevant preclinical model (Lordoz test).

| Group | Progesterone, mg/rat | Investigated drug, pig/rat | Number of proceptive behavior acts Day of giving the drug | | | |
|---|---|---|---|---|---|---|
| | | | 0 | 5 | 11 | 16 |
| Thr-Lys-Pro | 0.5 | 100 | 14 ± 4 | 15 ± 4 | 20 ± 4 | 28 ± 4 |
| Thr-Lys-Hyp | 0.5 | 100 | 12 ± 4 | 25 ± 4 | 24 ± 4 | 26 ± 4 |
| Thr-Lys-Pro-Arg-Pro (SEQ ID NO: 6) | 0.5 | 100 | 12 ± 4 | 15 ± 4 | 24 ± 4 | 36 ± 6 |
| Thr-Lys-Hyp-Arg-Hyp (SEQ ID NO: 12) | 0.5 | 100 | 13 ± 4 | 38 ± 4 | 36 ± 4 | 36 ± 6 |
| Thr-Lys-Pro-Arg-Pro-Phe (SEQ ID NO: 7) | 0.5 | 100 | 14 ± 4 | 16 ± 4 | 19 ± 4 | 26 ± 4 |
| Thr-Lys-Hyp-Arg-Hyp-Phe (SEQ ID NO: 13) | 0.5 | 100 | 14 ± 4 | 24 ± 4 | 23 ± 4 | 24 ± 4 |

Moreover, if one compares the data obtained in dynamic manner (comparing of the proceptive behavior of the female rats on day 5, 11 and 16 of administering the peptides), It is evident that the effect from the action of the peptides of the invention develops twice as fast as that from the action of the peptides described in RU2507212 (FIG. 1-3).

Thus, the data obtained testify to the fact that the peptides of the invention containing hydroxyproline not only have a greater stability as compared to the peptide analogues from RU2507212, but also have a higher rate of achieving a positive (therapeutic) effect, which in turn makes it possible to shorten the treatment course of the patient by using a pharmaceutical based on the peptides of the invention. Moreover, the effect is specific and is manifested in an adequate behavioral situation.

Even though the invention has been specified with reference to the variant embodiments disclosed, it will be evident to the person skilled in the art that the specific experiments described in detail are given merely for purposes of illustrating the present invention and should not be considered as limiting the scope of the invention in any way. It should be understood that it is possible to make various modifications without departing from the essence of the present invention.

The invention claimed is:

1. A peptide consisting of formula (I):

A-Thr-Lys-Hyp-B-C-D-X (SEQ ID NO: 8)    formula (I), or its pharmaceutically acceptable salt, wherein
A is absent, Met, Met(O), Thr, Ala, His, Phe, Lys, or Gly;
B is absent, Gly, Asp, Trp, Gln, Asn, Tyr, Hyp, or Arg;
C is absent, Arg, Phe, Tyr, Gly, His, Hyp, or Lys;
D is absent, Val, Gly, Tyr, Trp, Phe, or His;
X is OH, $OCH_3$, or $NH_2$ group;
provided that
(i) when A is present, at least one of B, C, or D is also present, or when B is present, then C and/or D is also present and (ii) the peptide is not a tetrapeptide.

2. A pharmaceutical composition comprising the peptide of claim 1 or a pharmaceutically acceptable salt thereof and at least one pharmaceutically acceptable excipient, wherein said peptide is present in the composition in an amount effective for stimulating sexual and genital function.

3. The pharmaceutical composition of claim 2, wherein the pharmaceutically acceptable excipient is a vehicle, a preservative, and/or a solvent.

4. The pharmaceutical composition of claim 2, wherein said composition is formulated in a liquid dosage form.

5. The pharmaceutical composition of claim 4, wherein the liquid dosage form is a solution for intranasal administration.

6. The pharmaceutical composition of claim 5, comprising 2 to 20 g/l of the peptide and 0.095 to 0.105 g/l of benzalkonium chloride.

7. The pharmaceutical composition of claim 2, comprising 2 to 20 g/l of the peptide and 0.095 to 0.105 g/l of benzalkonium chloride.

8. The pharmaceutical composition of claim 2, wherein said composition is formulated in a spray for intranasal administration.

9. The peptide of claim 1 or its pharmaceutically acceptable salt, wherein
A is absent;
B is Arg;
C is Arg, Phe, Tyr, Gly, His, Hyp, or Lys, and
D is absent.

10. The peptide of claim 9, wherein the peptide is Thr-Lys-Hyp-Arg-Hyp-X (SEQ ID NO: 12) or a pharmaceutically acceptable salt thereof.

11. The peptide of claim 1, wherein the peptide is Thr-Lys-Hyp-Arg-Hyp-Phe-X (SEQ ID NO: 13) or a pharmaceutically acceptable salt thereof.

12. The peptide of claim 1, wherein the peptide is Thr-Lys-Hyp-X or a pharmaceutically acceptable salt thereof.

* * * * *